United States Patent
Jacofsky (10) Patent No.: US 9,472,382 B2
(45) Date of Patent: Oct. 18, 2016

(54) COLD PLASMA ANNULAR ARRAY METHODS AND APPARATUS

(71) Applicant: Plasmology4, Inc., Scottsdale, AZ (US)

(72) Inventor: Marc C. Jacofsky, Phoenix, AZ (US)

(73) Assignee: Plasmology4, Inc., Scottsdale, AZ (US)

(*) Notice: Subject to any disclaimer, the term of this patent is extended or adjusted under 35 U.S.C. 154(b) by 261 days.

(21) Appl. No.: 14/145,312

(22) Filed: Dec. 31, 2013

(65) Prior Publication Data

US 2014/0184072 A1 Jul. 3, 2014

Related U.S. Application Data

(60) Provisional application No. 61/747,428, filed on Dec. 31, 2012.

(51) Int. Cl.
*H02J 7/24* (2006.01)
*H01J 37/32* (2006.01)

(52) U.S. Cl.
CPC .... *H01J 37/32899* (2013.01); *H01J 37/32082* (2013.01)

(58) Field of Classification Search
CPC ............... H01J 37/32899; H01J 37/32082; A61N 5/0616; A61N 1/306
USPC ............... 315/111.21, 111.51; 604/501, 23; 606/41; 128/845
See application file for complete search history.

(56) References Cited

U.S. PATENT DOCUMENTS

| | | | |
|---|---|---|---|
| 2,927,322 A | 3/1960 | Simon et al. |
| 3,432,722 A | 3/1969 | Naydan et al. |
| 3,487,414 A | 12/1969 | Booker |
| 3,735,591 A | 5/1973 | Burkhart |
| 4,088,926 A | 5/1978 | Fletcher et al. |
| 4,365,622 A | 12/1982 | Harrison |
| 4,380,320 A | 4/1983 | Hollstein et al. |
| 4,422,013 A | 12/1983 | Turchi et al. |
| 5,079,482 A | 1/1992 | Villecco et al. |
| 5,216,330 A | 6/1993 | Ahonen |
| 5,225,740 A | 7/1993 | Ohkawa |

(Continued)

FOREIGN PATENT DOCUMENTS

| WO | WO 2005/084569 A1 | 9/2005 |
|---|---|---|
| WO | WO 2006/116252 | 11/2006 |

(Continued)

OTHER PUBLICATIONS

Misra et al., "Nonthermal Plasma Inactivation of Food-Borne Pathogens," *School of Food Science and Environmental Health at Dublin Institute of Technology*, 32 pages (2011).

(Continued)

*Primary Examiner* — Lincoln Donovan
*Assistant Examiner* — Thomas Skibinski
(74) *Attorney, Agent, or Firm* — Sterne, Kessler, Goldstein & Fox P.L.L.C.

(57) ABSTRACT

Methods and apparatus are described that use an array of two or more cold plasma jet ports oriented to converge at a treatment area. The use of an array permits greater tissue penetration by cold plasma treatments. This approach enables treatment of deeper infections of soft and hard tissues without surgical intervention. For example, this approach can treat sub-integumental infections, such as those common to joint replacements, without surgically opening the issues overlying the deeper infection.

24 Claims, 5 Drawing Sheets

(56) References Cited

U.S. PATENT DOCUMENTS

| | | | |
|---|---|---|---|
| 5,304,888 A | 4/1994 | Gesley et al. | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A | 10/1999 | Selwyn | |
| 5,977,715 A | 11/1999 | Li et al. | |
| 6,096,564 A | 8/2000 | Denes et al. | |
| 6,099,523 A | 8/2000 | Kim et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,278,241 B1 * | 8/2001 | Enguelcht | H05H 1/44 219/121.52 |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,608,839 B2 | 10/2009 | Coulombe et al. | |
| 7,633,231 B2 | 12/2009 | Watson | |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,267,884 B1 | 9/2012 | Hicks | |
| 8,294,369 B1 | 10/2012 | Laroussi | |
| 8,460,283 B1 | 6/2013 | Laroussi et al. | |
| 2002/0129902 A1 | 9/2002 | Babayan et al. | |
| 2003/0222586 A1 | 12/2003 | Brooks et al. | |
| 2005/0088101 A1 | 4/2005 | Glidden et al. | |
| 2005/0179395 A1 | 8/2005 | Pai | |
| 2006/0189976 A1 | 8/2006 | Karni et al. | |
| 2008/0159925 A1 | 7/2008 | Shimizu et al. | |
| 2009/0188626 A1 | 7/2009 | Lu et al. | |
| 2010/0133979 A1 | 6/2010 | Lu | |
| 2011/0022043 A1 | 1/2011 | Wandke et al. | |
| 2012/0100524 A1 | 4/2012 | Fridman et al. | |
| 2012/0187841 A1 | 7/2012 | Kindel et al. | |
| 2012/0259270 A1 | 10/2012 | Wandke et al. | |
| 2013/0022514 A1 | 1/2013 | Morfill et al. | |
| 2013/0053762 A1 | 2/2013 | Rontal et al. | |
| 2013/0134878 A1 | 5/2013 | Selwyn | |
| 2013/0199540 A1 | 8/2013 | Buske | |
| 2014/0000810 A1 | 1/2014 | Franklin et al. | |

FOREIGN PATENT DOCUMENTS

| | | |
|---|---|---|
| WO | WO 2007/124910 A2 | 11/2007 |
| WO | WO 2010/107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http//www.physorg.com/printnews.php?newsid=6688>.

Book of Abstracts, 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, WILEY-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

Fridman et al., "Comparison of Direct and Indirect Effects of Non-Thermal Atmospheric-Pressure Plasma on Bacteria," *Plasma Processl Polym.*, 4, 370-375, 6 pages, WILEY-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd ( Mar. 2010).

U.S. Appl. No. 61/485,747, filed May 13, 2011, inventor Thomas J. Sheperak, 14 pages.

Liu et al., "Sub-60°C atmospheric helium-water plasma jets: modes, electron heating and downstream reaction chemistry," *J. Phys. D: Appl. Phys.* 44 345203, 13 pages, IOP Publishing Ltd. (Aug. 11, 2011).

Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

(56) References Cited

OTHER PUBLICATIONS

Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).

Dobrynin, et al., "Live Pig Skin Tissue and Wound Toxicity of Cold Plasma Treatment," *Plasma Medicine*, 1(1):93-108, 16 pages, Begell House, Inc. (2011).

Fernández, et al., "The inactivation of *Salmonella* by cold atmosphere plasma treatment," *Food Research International*, 45:2, 678-684, 7 pages, Elsevier Ltd. (Mar. 2012).

Tien, et al., "The Bilayer Lipid Membrane (BLM) Under Electrical Fields," *IEEE Transactions on Dielectrics and Electrical Institute*, 10:5, 717-727, 11 pages (Oct. 2003).

Jayaram, et al.., "Optimization of Electroporation Waveforms for Cell Sterilization," *IEEE Transactions on Industry Applications*, 40:6, 1489-1497, 9 pages (2004).

Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).

Fridman, et al., "Use of Non-Thermal Atmospheric Pressure Plasma Discharge for Coagulation and Sterilization of Surface Wounds," 6 pages (Jun. 2005).

Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).

Gurol, et al., "Low Temperature Plasma for decontamination of *E. coli* in milk," *International Journal of Food Microbiology*, 157:1-5, 5 pages, Elsevier B.V. (Jun. 2012).

Lado, et al., "Alternative food-preservation technologies: efficacy and mechanisms," *Microbes and Infection*, 4: 433-440 8 pages, Elsevier SAS (2002).

Leduc, et al., "Cell permeabilization using a non-thermal plasma," *New Journal of Physics*, 11: 115021, 12 pages, IOP Publishing Ltd and Deutsche Physikalische Gesellschaft (2009).

Machado, et al., "Moderate electric fields can inactivate *Escherichia coli* at room temperature," *Journal of Food Engineering*, 96: 520-527, 8 pages, Elsevier Ltd. (2009).

Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).

Morfill, et al., "Nosocomial infections-a new approach towards preventive medicine using plasmas," *New Journal of Physics*, 11: 115019, 10 pages, IOP Publishing Ltd and Deutsche Physikalische Gesellschaft (2009).

Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).

Toepfl, et al., "High intensity pulsed electric fields applied for food preservation," *Chemical Engineering and Processing*, 46: 537-546, 10 pages, Elsevier B.V. (2007).

\* cited by examiner

FIG. 5

COLD PLASMA ANNULAR ARRAY METHODS AND APPARATUS

CROSS-REFERENCE TO RELATED APPLICATIONS

This application claims the benefit of U.S. Provisional Application No. 61/747,428, filed Dec. 31, 2012 and entitled "Cold Plasma Toroidal Array Methods and Apparatus," which is incorporated herein by reference in its entirety.

This application is related to U.S. Provisional Application No. 60/913,369, filed Apr. 23, 2007; U.S. patent application Ser. No. 12/038,159, filed Feb. 27, 2008 (which issued as U.S. Pat. No. 7,633,231); U.S. patent application Ser. No. 13/620,118, filed Sep. 14, 2012; and U.S. patent application Ser. No. 14/026,679, filed Sep. 13, 2013, each of which are herein incorporated by reference in their entireties.

BACKGROUND

1. Field of the Art

The present invention relates to devices and methods for cold plasma application, and, more particularly, to arrays of such devices that are formed in an annular shape and methods for using same.

2. Background Art

When infections of deep tissues occur in the body it is often necessary to perform a surgical procedure to expose the infection, manually clean or debride the site, pack it with antibiotics, and initiate systemic antibiotics in an attempt to resolve the infection. In the case of orthopedic infections, where there is hardware of metallic or plastic composition present, the standard course of treatment may require multiple surgical procedures. Since the hardware may be covered in bacterial colonies and there is limited vascularization of the tissues immediately contacting the hardware, the colonization of the hardware often can't be controlled with systemic antibiotic use alone. In the case of an infected total joint replacement, the surgeon will often perform a "two-stage revision" procedure. The first stage involves opening the joint, removing the hardware, debriding infected tissue, packing the region with antibiotic impregnated materials, and closing the incision. Along with systemic antibiotics, the antibiotic materials are left in the patient, often with a non-functional joint complex, for on average 6 weeks. After blood and joint fluid tests suggest resolution of the infection, a second procedure is performed to remove the antibiotic laden materials and implant a new functional joint replacement. In some cases the infection is still present locally even though blood indicators are normal, and the new implant may quickly become re-infected, starting the "2-stage revision" procedure over again. In extreme cases, amputation may be the prescribed course of action for severe extremity infections that fail to resolve after these measures.

It is therefore highly desirable to be able to eradicate a deep joint infection without the need for repeated surgeries and a reliance on antibiotics to reach the site either through the circulatory system or by local, internal, long-term application. The same applies to other bone and deep tissue infections, abscesses, and similar conditions familiar to those in the medical field. As cold plasmas also show promise in the treatment of malignant growths, this array would have use in the treatment of deep tissue tumors, or any disorder that requires greater depth of penetration of plasma, including musculoskeletal pain and inflammation.

BRIEF SUMMARY OF THE INVENTION

An embodiment is described of an apparatus having an annular structure with two or more cold plasma devices located on the annular structure and directed internal to the annular structure so as to converge at a treatment area. The two or more cold plasma devices are coupled to one or more high voltage RF ports and to one or more gas supply ports.

A further embodiment is described of a method of producing cold plasma for use in a medical treatment. The method includes receiving, from a cold plasma power supply, electrical energy at two or more cold plasma devices via one or more high voltage RF ports. The two or more cold plasma devices are located on an annular structure. The method also includes receiving, from a gas source, gas at the two or more cold plasma devices via one or more gas supply ports. Finally, the method includes outputting cold plasma from the two or more cold plasma devices, the cold plasma from these cold plasma devices being directed to converge at a treatment area.

DETAILED DESCRIPTION OF THE INVENTION

Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, tumor treatments, anti-inflammatory treatments, non-infective disorders that may be treatable with cold plasmas, and various other medical therapies and sterilization.

Conventional cold plasma treatments were focused on treatment areas at the surface of the skin, as it was not previously known that cold plasmas could penetrate the surface of the skin. Consequently, no contemplation was previously considered as to approaches by which cold plasma penetration for treatment purposes could be improved or optimized. However, recent data that is described in U.S. patent application Ser. No. 14/026,679, entitled "Therapeutic Applications of Cold Plasma," filed Sep. 13, 2013, indicate that subcutaneous treatment protocols are feasible with cold plasmas. In particular, paragraphs [0084]-[0089] of this referenced application provide data in support of the proposition that cold plasma penetrates beneath the skin so that internal tissue treatments are feasible.

Consideration of the penetration effects of cold plasma indicates that the penetration can be thought of as a cone of attenuation below the skin surface. The cold plasma intensity decreases due to the spreading effect associated with the conical penetration shape below the skin surface. It is therefore desirable to be able to increase the penetration and/or to increase the intensity at various depths below the surface of the skin. By generating multiple "cones" of treatment in the tissues, with some degree of overlap, the desirable effects in deep tissues can be amplified. Therefore, increasing the intensity at various targeted depths below the skin surface, the volumetric problem of certain internal tissues disorders can be addressed.

Figure 1:
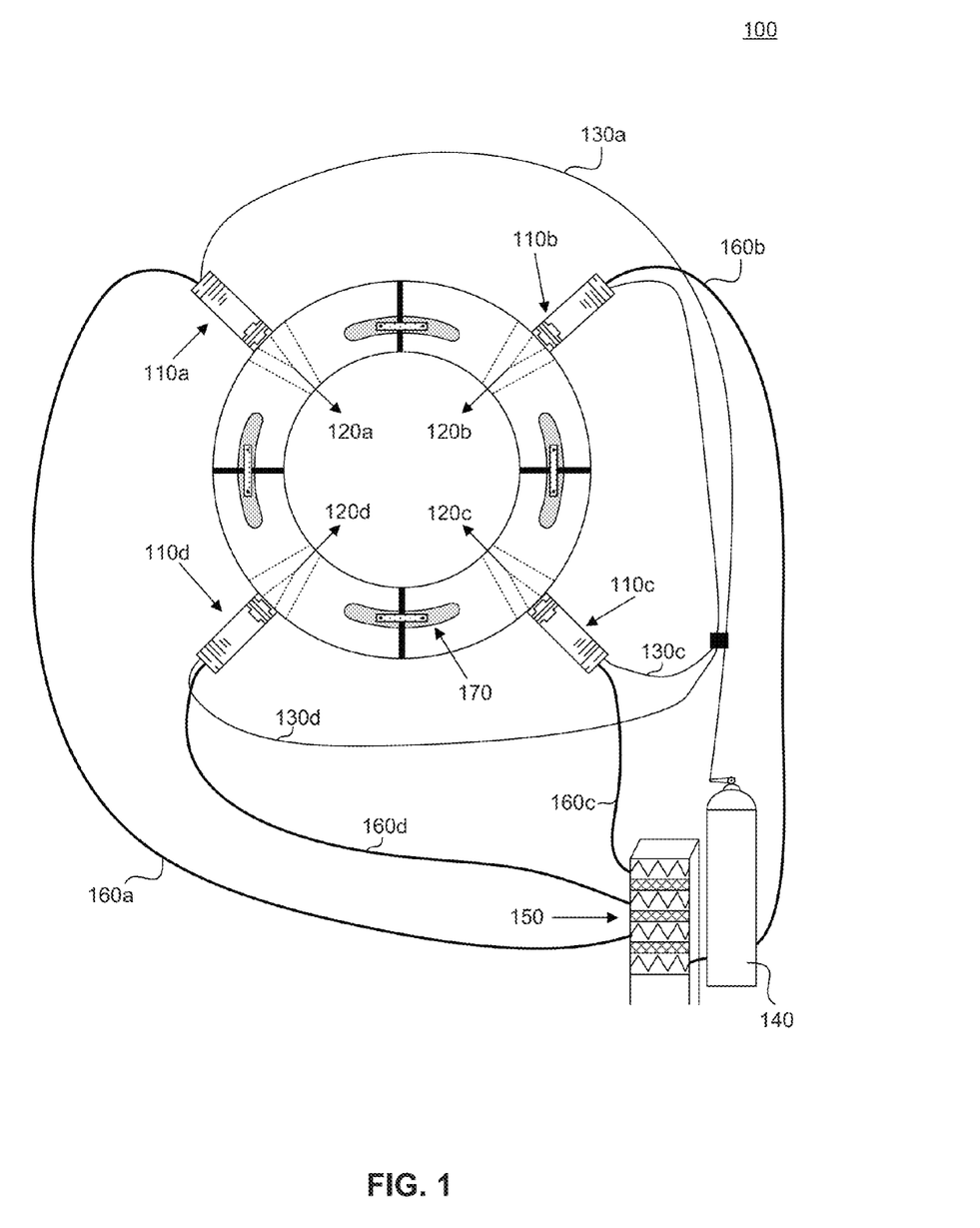
FIG. 1 illustrates an embodiment of the cold plasma annular treatment device that includes an array of a plurality of plasma ports.

Embodiments of the present disclosure include an annular device designed with an array of two or more individual cold plasma (CP) jet ports oriented to converge about a patient's body segment (either at the skin surface or below the skin surface) resulting in a plurality of treatment angles (FIG. 1). The effective penetration of a typical cold plasma jet is generally on the order of <2 cm. By arranging a plurality of jets circumferentially around the desired treatment zone, penetration to deeper tissues is possible and more complete. Embodiments of the cold plasma annular treatment device can be used to treat sub-integumental infections, such as abscess, bone, and joint infections, without surgically opening the tissues overlying the deeper infection. The ability to treat deep infections of the soft and hard tissues of the body without surgical intervention greatly reduces the risk of secondary complications (comorbidities), reduces pain, and decreases the cost of treating these infections. Other beneficial applications of cold plasma, such as treating tumors or musculoskeletal disorders would also benefit from improved penetration.

Figure 2:
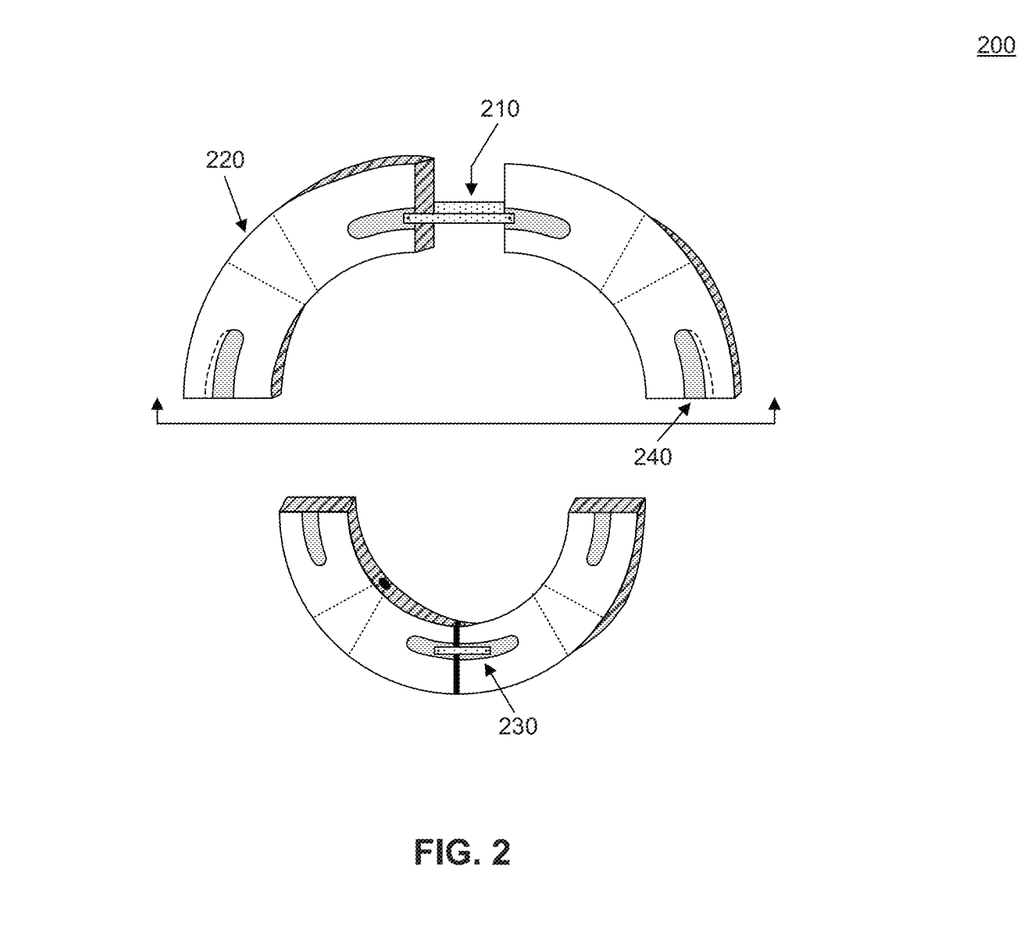
FIG. 2 illustrates an embodiment that provides an adjustable four-port array of a plurality of cold plasma ports in an annular orientation.

The device, designed similarly to a modern magnetic resonance imaging (MRI) machine, allows the patient's injured or infected segment to be placed inside of the machine, which is designed in an annular shape to surround the affected area, FIG. 2 illustrates an adjustable symmetrical array of cold plasma ports surround the segment to apply a treatment of the desired duration and intensity. The array could consist of any number of ports (FIG. 1, for example, illustrates 4 ports, but two or more ports are contemplated to be within the scope of the present disclosure) to expand the degree of coverage of treatment through an overlapping and/or converging plurality of plasma jets. The annular array could be molded in unique sections, such as four sections (FIG. 2) and assembled after manufacture. The ports themselves can be designed and manufactured to each provide a cold plasma jet, using any approach known to one skilled in the art. As an example (which is not intended to be limiting), the cold plasma jet sources may be the multi-frequency harmonic-rich cold plasma (MFHCP) devices described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"), which are incorporated herein by reference. Included in the description in U.S. Pat. No. 7,633,231 are devices that form cold plasma without the use of internal ground electrodes. Furthermore, the high voltage RF power supply may be (but not limited to) that described in the '369 patent family, or in U.S. patent application Ser. No. 13/620,118, filed Sep. 14, 2012, which is also incorporated herein by reference. In both the cold plasma device and high voltage RF power supply, the scope of this invention is not limited to these particular examples, but covers all cold plasma devices and high voltage RF power supplies.

On the cold plasma annular treatment device, the devices would be activated remotely by a common trigger mechanism to generate plasma. This common trigger mechanism could be a physical flow control or a computer console that triggers a plurality of valves and RF energy. The devices would be affixed to the annular array, as illustrated for example in FIG. 1.

FIG. 1 illustrates an embodiment of the cold plasma annular treatment device that includes a symmetrical array of a plurality of plasma ports. In this embodiment, four (4) ports 120a, 120b, 120c, 120d are illustrated, although two or more ports falls within the scope of various embodiments of the present invention. Attached to each port is a cold plasma generation unit 110a, 110b, 110c, 110d with the plasma flow directed as shown to converge at an interior region. Each cold plasma generation unit 110 is connected by a high-voltage RF feed cable 160 to one or more high voltage RF power supplies 150, and a gas supply line 130 to a suitable supply of gas 140. The cold plasma annular treatment structure can be modified to fit the appropriate size permitted by the each of the plasma ports, as well as the intended treatment area. A sliding/locking mechanism 170 is illustrated that allows the cold plasma annular treatment structure to expand or contract as necessary to make the appropriate physical accommodation. The high voltage RF power supplies can be similar to those described in the '369 application family.

FIG. 2 illustrates an embodiment that provides an adjustable four-port array of a plurality of cold plasma ports 220 in an annular orientation. Since the distance between the plasma outlet port and treatment target are critical for effective treatment and tissue penetration, the internal treatment area of the array can be adjusted to optimize the distance between the plasma outlet ports and the target area (e.g., a patient's body segment) undergoing treatment. Sliding/locking mechanism 170 may be in an open position 210, or in a closed position 230. Sliding/locking mechanism 170 makes use of an adjustment track 240. The array can be expanded or contracted as needed, and locked into place to ensure consistent and optimized treatment distances. As can be readily surmised by an examination of the Figures, the array can be adjusted in one direction, or in a second direction. The second direction can be orthogonal, or at another suitable angle, to the first direction. Such adjustment directions are merely exemplary, and serve to illustrate the flexibility of adjustment envisaged for various embodiments within the scope of the present invention.

Figure 3:
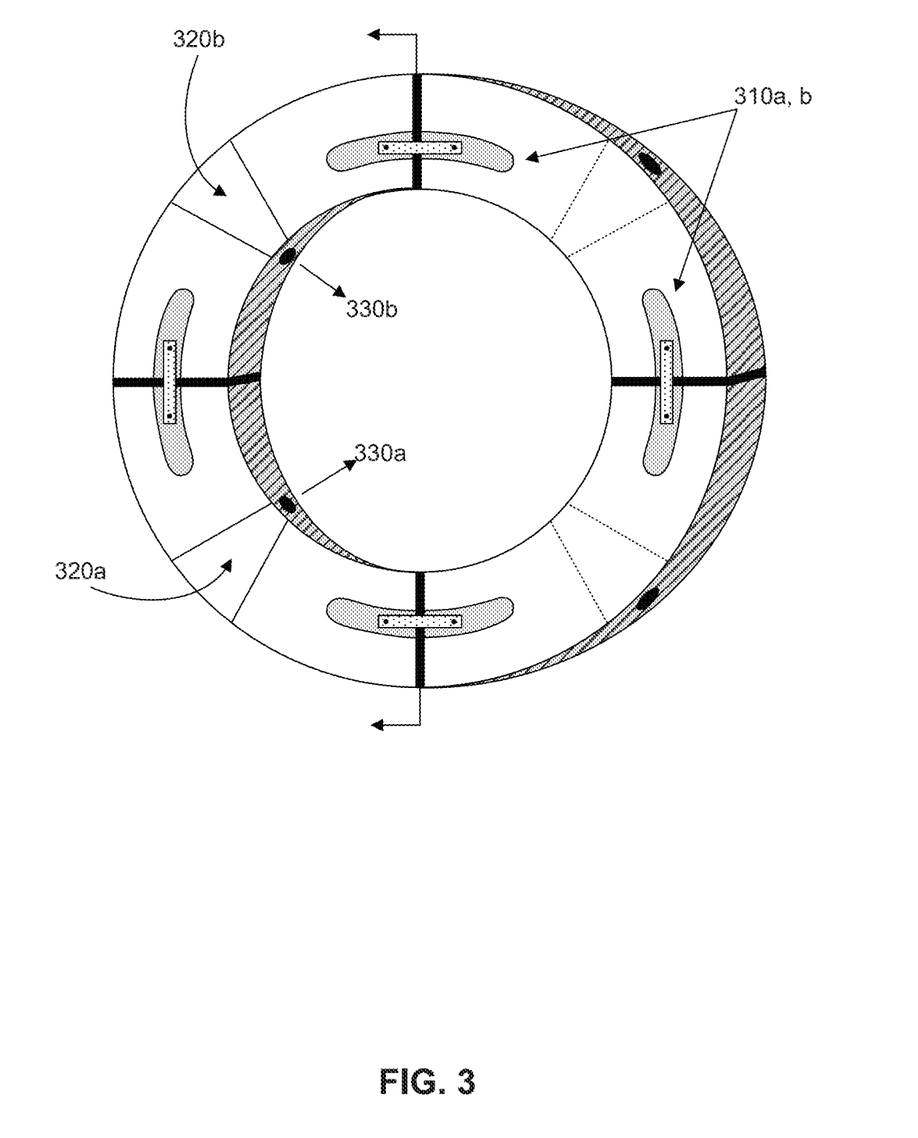
FIG. 3 illustrates an embodiment of a four-port, adjustable array (in a closed position) of a plurality of cold plasma ports in an annular orientation.

FIG. 3 illustrates an embodiment of a four-port, adjustable symmetrical array (in a closed position using sliding/locking mechanism 310) of a plurality of cold plasma ports in an annular orientation. Although FIG. 3 illustrates the possibility of four ports, only two ports 320a, 320b are occupied for this particular treatment regime. As expected, cold plasma 330a, 330b emanates and converges to a treatment area (not shown). In this embodiment, the two cold plasma sources are on the same side of the treatment area.

Figure 4:
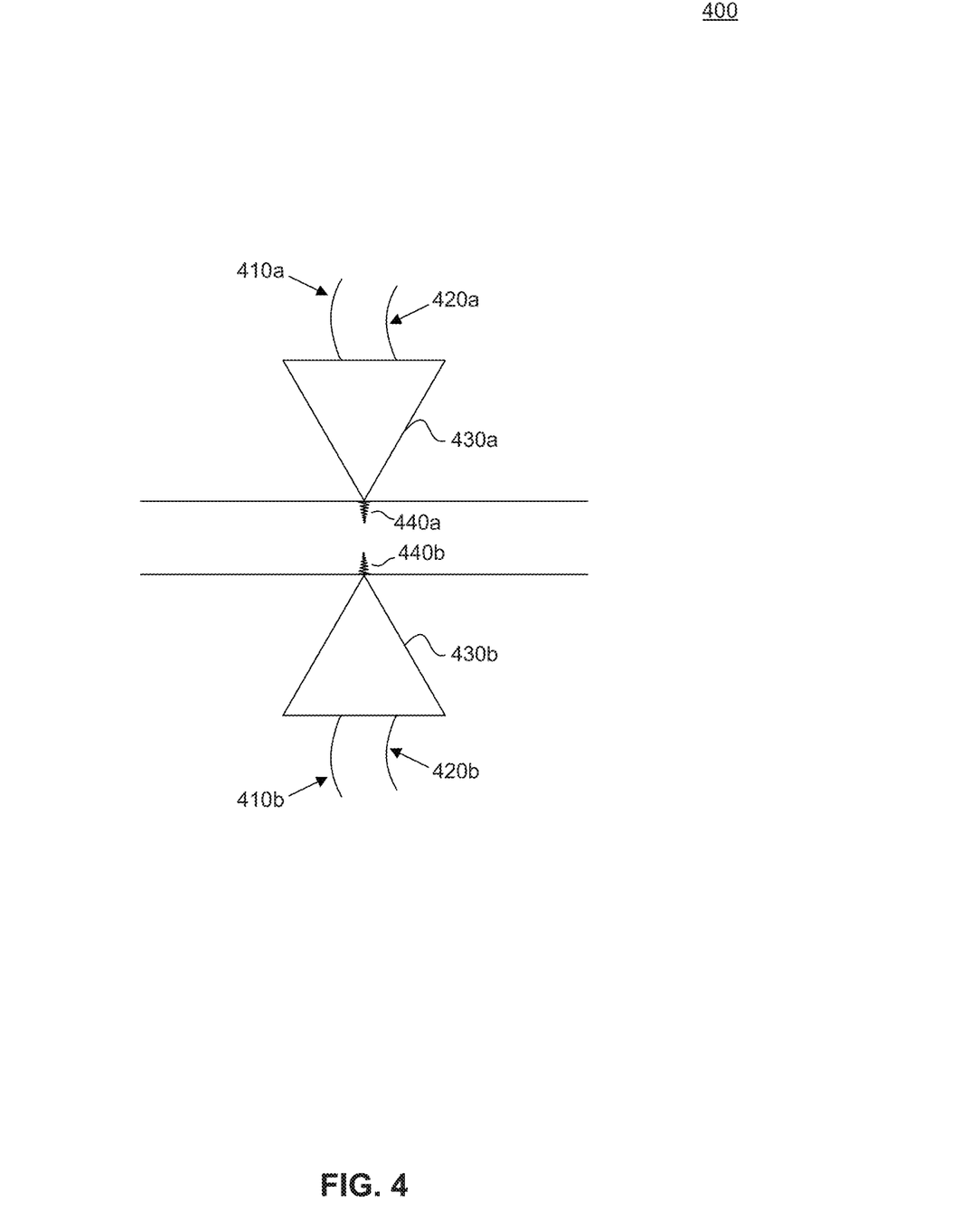
FIG. 4 illustrates an embodiment where two cold plasma ports are positioned to be diametrically opposed to one another, with convergence of the resulting cold plasma jets occurring between the two cold plasma ports.

In the context of this application, an annular cold plasma structure includes the scenario where two cold plasma ports are aligned diametrically opposed to one another, with a treatment area located in between the two cold plasma ports to receive cold plasma from those two cold plasma ports. FIG. 4 illustrates such an embodiment, with cold plasma devices 430a, 430b positioned to be diametrically opposed to one another. Each cold plasma device 430 receives a source of electrical energy via high voltage RF feed line 420 and gas via gas feed line 410. Cold plasma 440a, 440b emanates from cold plasma devices 430a, 430b to reach treatment area (not shown) that is in between cold plasma devices 430a, 430b.

Figure 5:
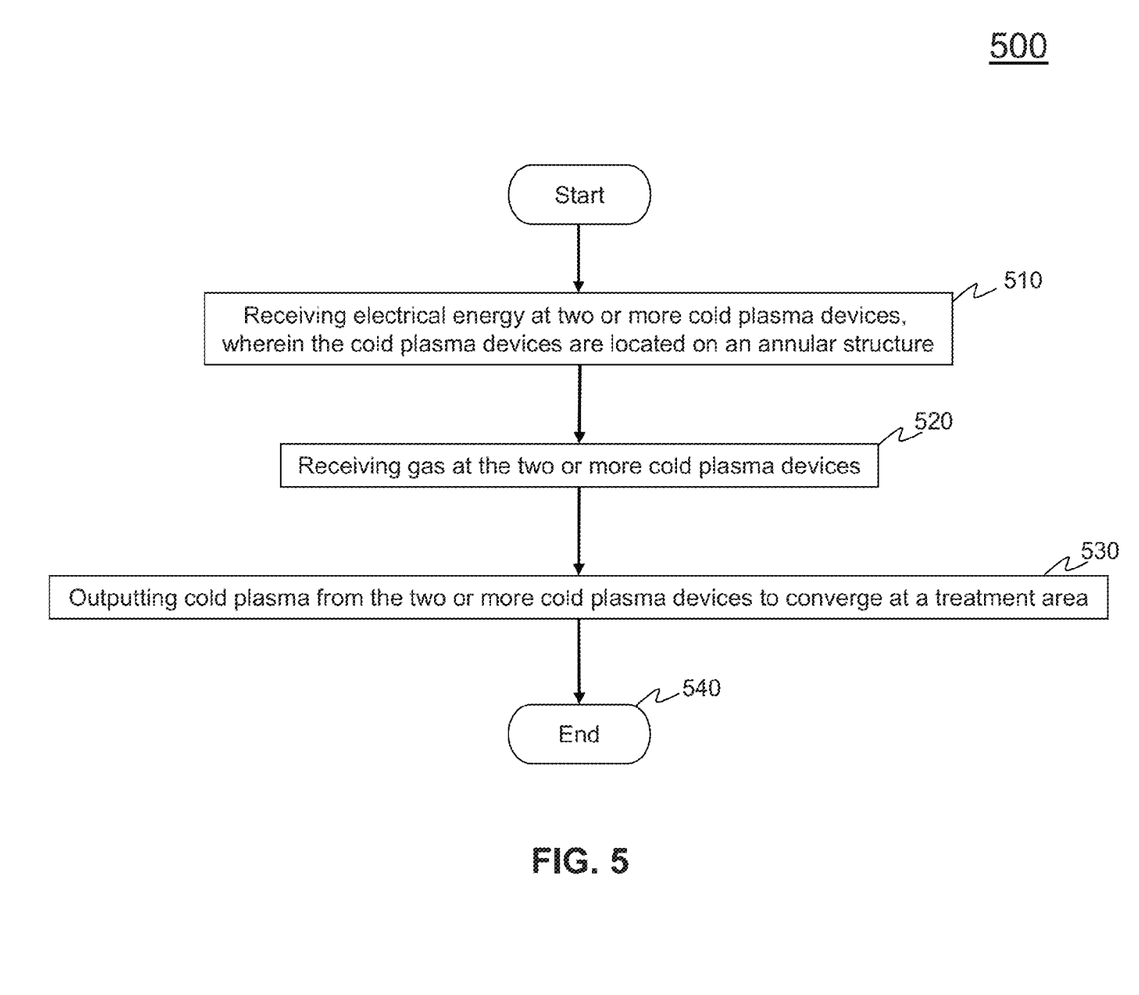
FIG. 5 illustrates a flowchart of a method for providing two or more cold plasma jets that converge at a treatment area, according to an embodiment of the present disclosure.

FIG. 5 provides a flowchart of a method for providing two or more cold plasma jets that converge at a treatment area, according to an embodiment of the present disclosure.

The process begins at step 510. In step 510, electrical energy is received at two or more cold plasma devices, wherein the cold plasma devices are located on an annular structure.

In step 520, gas is received at the two or more cold plasma devices.

In step 530, cold plasma is output from the two or more cold plasma devices so as to converge at a treatment area.

At step 540, method 500 ends.

Although the above description has used the '369 application family as the baseline cold plasma device, the scope of the present invention is not limited to the '369 application family baseline. The '369 application family baseline is merely exemplary and not limiting, and therefore embodiments of the present invention include the deployment of the above annular features to cold plasma generation devices in general, irrespective of their means of generation.

As noted above, the four-port configuration is exemplary, and not a limiting of various embodiments of the present invention. Other numbers of ports fall within the scope of various embodiments of the present invention. Further, although a symmetric configuration is described above, non-symmetric or asymmetric configurations of ports can also be used to provide a particular treatment protocol, and such non-symmetric/asymmetric configurations also fall within the scope of various embodiments of the present invention.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An apparatus comprising:
an annular structure having two or more cold plasma devices positioned to provide converging cold plasma jets that converge at a treatment area, wherein at least one of the two or more cold plasma devices is coupled to one or more high voltage RF power supplies.

2. The apparatus of claim 1, wherein the two or more cold plasma devices are positioned in a circumferential orientation.

3. The apparatus of claim 1, wherein the annular structure is configured to expand in a first direction.

4. The apparatus of claim 1, wherein the annular structure is configured to expand in a first direction and in a second direction.

5. The apparatus of claim 4, wherein the first direction and the second direction are orthogonal directions.

6. The apparatus of claim 1, wherein the two or more cold plasma devices are configured to generate two or more cold plasma jets that are diametrically opposed to one another, the treatment area being located between the two or more cold plasma devices.

7. The apparatus of claim 1, wherein the two or more cold plasma devices are coupled to a common triggering mechanism to simultaneously activate the two or more cold plasma devices.

8. The apparatus of claim 1, wherein functionality settings of the two or more cold plasma devices are independently configurable to provide a desired treatment regime at the treatment area.

9. The apparatus of claim 8, wherein the functionality settings of the two or more cold plasma devices include functionality settings by using computer control.

10. The apparatus of claim 1, wherein at least one of the two or more cold plasma devices is a multi-frequency harmonic-rich cold plasma device.

11. The apparatus of claim 1, wherein at least one of the two or more cold plasma devices is free of internal ground electrodes.

12. The apparatus of claim 1, wherein the annular structure is configured to surround the treatment area.

13. A method comprising:
receiving, from a cold plasma power supply, electrical energy at two or more cold plasma devices, wherein the two or more cold plasma devices are located on an annular structure, and wherein the cold plasma power supply is a harmonic high voltage RF power supply;
receiving, from a gas source, gas at the two or more cold plasma devices; and
outputting cold plasma from the two or more cold plasma devices to converge at a treatment area.

14. The method of claim 13, wherein the two or more cold plasma devices are located in a circumferential orientation.

15. The method of claim 13, wherein the annular structure is configured to expand in a first direction.

16. The method of claim 13, wherein the annular structure is configured to expand in a first direction and in a second direction.

17. The apparatus of claim 16, wherein the first direction and the second direction are orthogonal directions.

18. The method of claim 13, wherein outputting cold plasma from the two or more cold plasma devices includes outputting cold plasma in jets that are diametrically opposed to one another, the treatment area being located between the two or more cold plasma devices.

19. The method of claim 13, wherein the two or more cold plasma devices are coupled to a common triggering mechanism to simultaneously activate the two or more cold plasma devices.

20. The method of claim 13, wherein functionality settings of the two or more cold plasma devices are independently configurable to provide a desired treatment regime.

21. The method of claim 20, wherein the functionality settings of the two or more cold plasma devices include functionality settings by using computer control.

22. The method of claim 13, wherein at least one of the two or more cold plasma devices is a multi-frequency harmonic-rich cold plasma device, and outputting cold plasma includes outputting multi-frequency harmonic-rich cold plasma.

23. The method of claim 13, wherein receiving electrical energy at two or more cold plasma devices includes receiving electrical energy at at least one of the two or more cold plasma devices, wherein the at least one of the two or more cold plasma devices is free of internal ground electrodes.

24. The method of claim 13, wherein the annular structure is configured to surround the treatment area.

* * * * *